United States Patent
Lardaro et al.

(10) Patent No.: US 12,357,199 B2
(45) Date of Patent: Jul. 15, 2025

(54) HEARING EVALUATION SYSTEM

(71) Applicant: Otohub S.R.L., Naples (IT)

(72) Inventors: Gianna Lardaro, Naples (IT); Antonio Curci, Naples (IT)

(73) Assignee: AMPLIFON S.P.A., Milan (IT)

( * ) Notice: Subject to any disclaimer, the term of this patent is extended or adjusted under 35 U.S.C. 154(b) by 236 days.

(21) Appl. No.: 16/638,080

(22) PCT Filed: Aug. 10, 2018

(86) PCT No.: PCT/AU2018/050848
§ 371 (c)(1),
(2) Date: Feb. 10, 2020

(87) PCT Pub. No.: WO2019/028527
PCT Pub. Date: Feb. 14, 2019

(65) Prior Publication Data
US 2020/0178852 A1    Jun. 11, 2020

(30) Foreign Application Priority Data
Aug. 10, 2017 (AU) .................. 2017903191

(51) Int. Cl.
*A61B 5/12* (2006.01)
*G16H 40/67* (2018.01)
*H04R 25/00* (2006.01)

(52) U.S. Cl.
CPC ............. *A61B 5/123* (2013.01); *G16H 40/67* (2018.01); *A61B 5/128* (2013.01);
(Continued)

(58) Field of Classification Search
CPC ....... A61B 5/0051; A61B 5/123; A61B 5/128; A61B 5/1495; A61B 5/6898;
(Continued)

(56) References Cited

U.S. PATENT DOCUMENTS

2012/0288119 A1* 11/2012 Apfel .................. A61B 5/123
                                                              381/101
2013/0274628 A1* 10/2013 Fausti .................. A61B 5/123
                                                              600/559
(Continued)

FOREIGN PATENT DOCUMENTS

| JP | 2017042232 A * | 3/2017 | |
| WO | WO-2016024170 A1 * | 2/2016 | ........... A61B 5/0022 |
| WO | WO-2017158312 A1 * | 9/2017 | ........... A61B 5/0024 |

OTHER PUBLICATIONS

Thompson, et al. "Accuracy of a Tablet Audiometer for Measuring Behavioral Hearing Thresholds in a Clinical Population" Otolaryngology-Head and Neck Surgery, vol. 153(5) 838-842 (Year: 2015).*

(Continued)

*Primary Examiner* — Alex M Valvis
*Assistant Examiner* — Anna Roberts
(74) *Attorney, Agent, or Firm* — Troutman Pepper Locke LLP

(57) ABSTRACT

A portable hearing evaluation system is provided including: a portable computing device configured to provide audiometric testing of a patient according to one or more audiological standards; and a transducer, coupled to the portable computing device. The portable computing device is configured generate a plurality of test signals based at least in part according to one or more parameters and to be provided on an output of the portable computing device for playback on the transducer.

17 Claims, 7 Drawing Sheets

(52) U.S. Cl.
CPC .............. *A61B 2560/0228* (2013.01); *A61B 2560/0431* (2013.01); *A61B 2560/0462* (2013.01); *H04R 25/70* (2013.01)

(58) Field of Classification Search
CPC .......... A61B 5/7203; A61B 2560/0247; A61B 2560/0228; A61B 2560/0431; A61B 2560/0462; A61N 1/36036; G06Q 10/06311; G06Q 30/0271; G16H 15/00; G16H 20/00; G16H 40/67; H04R 25/70
See application file for complete search history.

(56) References Cited

U.S. PATENT DOCUMENTS

| | | | |
|---|---|---|---|
| 2015/0257683 A1* | 9/2015 | Ashmore | A61B 5/0022 600/559 |
| 2019/0045293 A1* | 2/2019 | Blau | A61B 5/0004 |

OTHER PUBLICATIONS

Rourke, et al. "Tablet Audiometry n Canada's North: A Portable and Efficient Method for Hearing Screening" 2016, Otolaryngology-Head and Neck Surgery, vol. 155(3) 473-478 (Year: 2016).*
International Search Report and Written Opinion for corresponding Application No. PCT/AU2018/050848 (mailed Nov 15, 2018).

* cited by examiner

HEARING EVALUATION SYSTEM

This application is a national stage application under 35 U.S.C. § 371 of PCT Application No. PCT/AU2018/050848, filed Aug. 10, 2018, which claims the priority benefit of Australian Patent Application No. 2017903191, filed Aug. 10, 2017.

TECHNICAL FIELD

The present invention relates to diagnosis of hearing impairments.

BACKGROUND ART

Audiometers are used by audiologists to test the hearing of patients to identify hearing impairments. In particular, the audiometer is a specialised device which generates tones (or other sounds), based upon input by the audiologist, and plays the tones to the patient. The patient then signals, e.g. by pushing a button, whether the tone (or other sound) is heard.

A problem with audiometers of the prior art is that they are expensive and bulky machines. In particular, it is costly to install an audiometer in a clinic, and it is difficult to transport audiometers between clinics. As such, access to audiometers is limited, particularly in remote communities.

Remote telehealth systems are often provided to patients in remote communities where patients and clinicians are able to communicate by videoconferencing. While such systems enable consultations that are general in nature, they do not allow reliable hearing assessment, or related diagnosis services, to be provided, particularly in low bandwidth environments.

It has long been desirable to enable preliminary hearing evaluations to be conducted at pharmacies, health centres and the like, without an audiologist. However, it is difficult to conduct this type of testing in such noisy environments. In particular, a soundproof booth is very costly and bulky, which is particularly problematic as floor space is often a premium in pharmacies. Furthermore, when testing is performed in such environments without a soundproof booth, the results are generally unreliable.

Another problem when testing is performed without an audiologist is that the test equipment is often not used correctly. As an illustrative example, transducers may be plugged in incorrectly, which is particularly prevalent when a patient is required to unplug and plug in different types of transducers to conduct the test.

It will be clearly understood that, if a prior art publication is referred to herein, this reference does not constitute an admission that the publication forms part of the common general knowledge in the art in Australia or in any other country.

SUMMARY OF INVENTION

The present invention is directed to hearing evaluation systems, which may at least partially overcome at least one of the abovementioned disadvantages or provide the consumer with a useful or commercial choice.

With the foregoing in view, the present invention in one form, resides broadly in a portable hearing evaluation system including:

a portable computing device configured to provide audiometric testing of a patient according to one or more audiological standards and thus function as a mobile audiometer; and a transducer, coupled to the portable computing device, wherein the portable computing device is configured generate a plurality of audiometric test signals based at least in part according to one or more parameters and to be provided on an output of the portable computing device for playback on the transducer.

Advantageously, the system enables hearing tests to be performed on patients without requiring a hardware audiometer. Furthermore, as the portable computing device produces stimuli without requiring a hardware audiometer, the hearing evaluation system is simplified, less expensive, and portable. Yet further again, as the portable computing device generates the plurality of audiometric test signals thereon, in contrast to playing pre-generated test signal files, the system can much more easily be calibrated to the one or more audiological standards.

The test signals may comprise test tones. The test signals may comprise speech stimuli.

Preferably, the test signals are calibrated for the transducer to one or more international audiological standards. Examples of such audiological standards include ANSI s3.6 or EN60645. As such, the portable computing device generates the plurality of audiometric test signals specific to the transducer.

Preferably, the system includes a trigger, for use by the patient, to signal that he or she has heard a test signal. The trigger may comprise a physical trigger. The trigger may comprise a button on a graphical user interface.

Preferably, the portable computing device includes a touchscreen with which the user may interact.

Preferably, the portable computing device includes a Tone Generator Engine (TGE) configured to generate a test signal of the plurality of test signals according to one or more input parameters. The input parameters may include a frequency and an amplitude.

The TGE may be configured to detect when a word is played, and adjust an output on the transducer according to whether a word is detected.

The TGE may be configured to enable the portable computing device to be calibrated for the transducer by extrapolating an amplitude change for a single amplitude across a plurality of amplitudes.

The TGE may be configured to use calibration data for each of a plurality of transducers. The calibration data may be stored locally on the portable computing device. Alternatively, the calibration data may be retrieved from a remote server.

Preferably, the portable computing device comprises a tablet computer. Alternatively, the portable computing device may comprise a smartphone, a laptop, a smartwatch, or smart speakers.

Preferably, the portable computing device includes a user interface, to enable an audiologist to select a test to be performed.

Preferably, the user interface enables the audiologist to specify characteristics of the test signals.

Preferably, the portable computing device is configured to generate an audiogram based upon patient responses, wherein the user interface includes the audiogram.

Preferably, the audiogram is generated based upon patient input.

Preferably, the system is configured to automatically generate a report based upon test data of the audiometric testing. The report may be generated according to a template. The template may be downloaded from a server.

The system may include a soundproof booth. The patient may be located within the soundproof booth during testing, and the portable computing device may be located outside of the soundproof booth.

The system may include a remote server, for storing test data.

The system may store patient information in the portable computing device. The patient information may be stored in compliance with one or more Privacy Regulations, such as but not limited to the Health Insurance Portability and Accountability Act (HIPAA) and the European General Data Protection Regulation (GDPR).

The system may include a plurality of portable computing devices at various locations, coupled to the remote server. The remote sever may be configured to send commands to each of the portable computing devices to conduct multiple hearing assessments. The commands sent to each of the portable computing devices may be different, to enable different hearing assessments to be conducted on each of the portable computing devices.

The remote server may comprise an electronic health record (EHR) store. The EHR store may store EHRs of a plurality of patients, and from a plurality of audiologists.

The remote server may be compliant with one or more privacy regulations, such as but not limited to Health Insurance Portability and Accountability Act (HIPAA) and the European General Data Protection Regulation (GDPR).

The remote server may be coupled to a common database server and/or virtual server, for use by fitting systems and suppliers. An example of such database is the NOAH database of HIMSA.

The system may be configured to provide remote audiometric testing of the patient.

The system may include a remote computing device, coupled to the portable computing device. The remote computing device may be configured to be used by the audiologist.

The remote computing device may be configured to send parameters to the portable computing device defining a test tone, wherein the portable computing device is configured to generate the test tone based upon the parameters.

Preferably, the portable computing device is configured to receive input from the patient regarding whether or not the patient has heard the test signal, and submit same to the remote computing device.

Preferably, the system includes video conferencing between the portable computing device and the remote computing device.

Preferably, the portable computing device and the remote computing device communicate with each other directly. If direct communication is interrupted, the portable computing device and the remote computing device may communicate through a server. Communication through the server may be temporary or permanent for a specific remote audiometry session.

The remote computing device may control multiple portable computing devices at the same time. Direct video and audio connection may be provided between the portable computing devices and the remote computing devices.

Preferably, data of the audiometric testing is used to program a hearing product. The programming of the hearing product may be performed through a wired or wireless connection from the remote computing device.

Preferably, the system includes a switch box, enabling a plurality of transducers to be coupled to the portable computing device. The switch box may include a wired or wireless connection with the portable computing device on which the test signals are received. The switch box may include a control link with the portable computing device on which control signals are received. The control signals may be used to activate a particular transducer of the plurality of transducers.

The portable computing device may be configured to enable the patient to initiate the test and provide feedback by interacting with the device directly. In such case, the portable computing device may be configured to provide automated testing. The testing may be carried out according to the Hughson-Westlake method.

The portable computing device may be configured to enable the patient to book an appointment with a hearing professional through the device itself and/or place an order of a hearing product. The hearing product may comprise a hearable, a hearing aid, an over the counter (OTC) hearing aid, a public safety answering point (PSAP), a personal sound amplification device (PSAD), or a hearing protection device.

The system may be configured to detect background noise. The system may determine whether test conditions are acceptable based on the background noise. The system may make compensating adjustments to the test data based upon the background noise. The system may be configured to conduct background noise measurements using a microphone. The microphone may be built-in to the portable computing device, or an external microphone. The system may be configured to detect broadband or narrowband background noise. The narrowband background noise be defined according to stimulus of the audiometric testing. The narrowband background noise may be defined around a central frequency for each of a plurality of stimuli frequencies.

The transducers may comprise wired or wireless earbuds and/or hearables devices. The transducers may comprise active noise cancelling transducers.

Data obtained by audiometric testing of a patient using wired or wireless earbuds and/or hearable devices may be used to fit a hearing device to compensate for hearing loss of the patient.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which.

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way.

DESCRIPTION OF EMBODIMENTS

Figure 1:
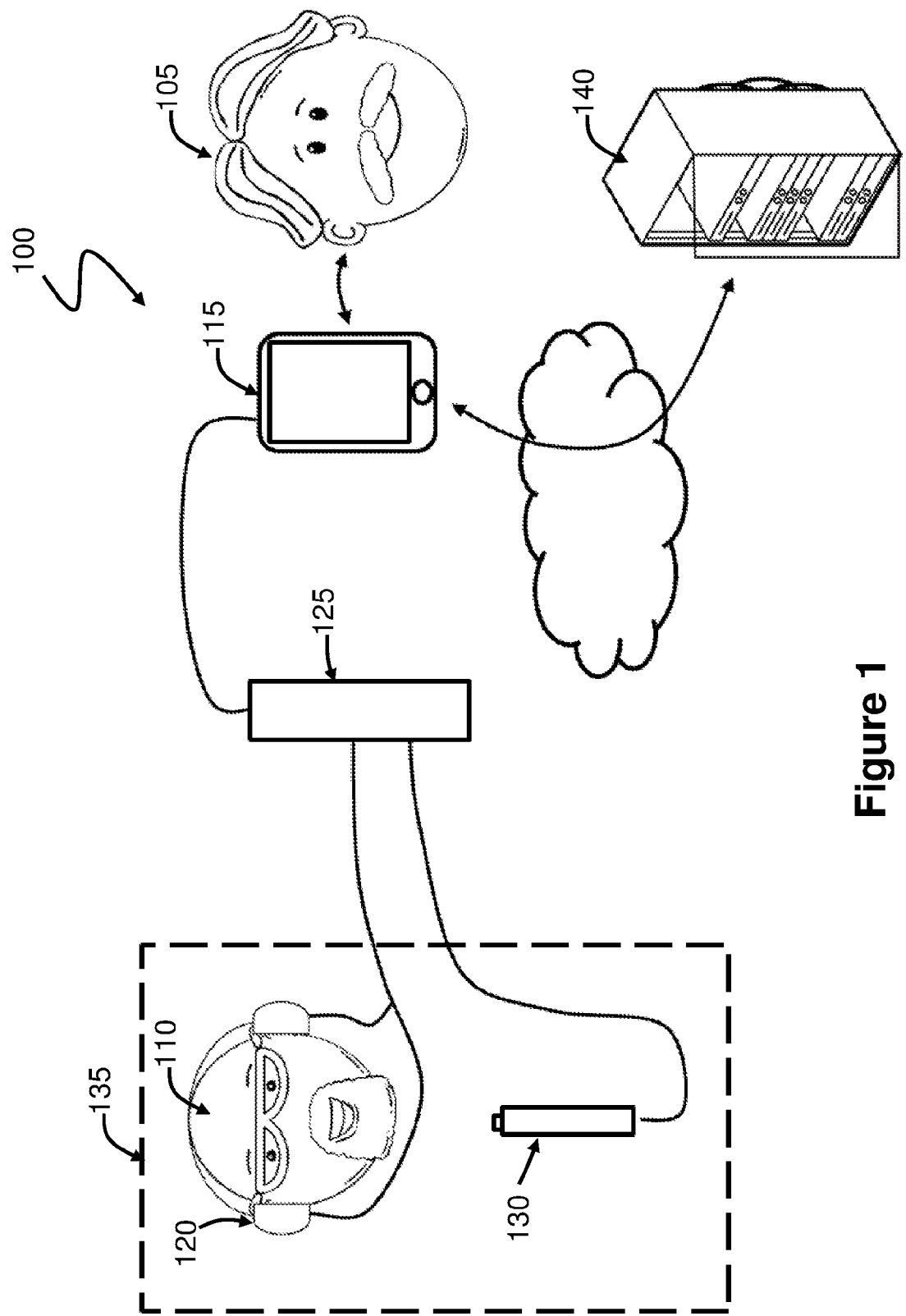
FIG. 1 illustrates a hearing evaluation system, for diagnosing hearing impairments, according to an embodiment of the present invention.

FIG. 1 illustrates a hearing evaluation system 100, for diagnosing hearing impairments, according to an embodiment of the present invention. The hearing evaluation system 100 enables audiologists 105 to conduct hearing tests on patients 110, without requiring a hardware audiometer.

In particular, the system 100 includes a mobile audiometer device 115, in the form of a tablet computer including software thereon, configured to provide audiometric testing according to one or more audiological standards. The mobile audiometer device 115 is advantageously portable and less expensive than a traditional audiometer, which enables it to be used more broadly.

In use, a transducer 120 is worn by the patient 110, and the transducer 120 is coupled to the mobile audiometer device 115 by a junction box 125. The mobile audiometer device 115 is configured to provide test signals (e.g. test tones) to the patient 110 using the transducer 120.

Furthermore, a trigger device 130 is coupled to the mobile audiometer device 115 by the junction box 125, and is used by the patient to signal that he or she has heard a test signal. The junction box 125, as outlined in further detail below, enables different types of transducers to be coupled to the mobile audiometer device 115 simultaneously.

The patient 110 is tested while inside a soundproof booth 135, to prevent background noise from influencing the test results, as is commonly done in the art of audiological testing. However, as outlined below, embodiments of the invention do not necessarily utilise a booth.

In use, the audiologist 105 interacts with the mobile audiometer device 115 to initially choose (or enter details of) the patient 110. This enables the test results to be saved in association with the patient, and a test report to be generated, as outlined below.

The audiologist 105 then selects a test to be performed using the mobile audiometer device 115. This is advantageously performing using a menu of tests which are available to the audiologist 105. Over the course of a hearing test with a patient, multiple tests may be selected. These tests may be selected initially, and then performed one after the other, or sequentially, where the audiologist 105 selects tests one after the other.

Figure 2:
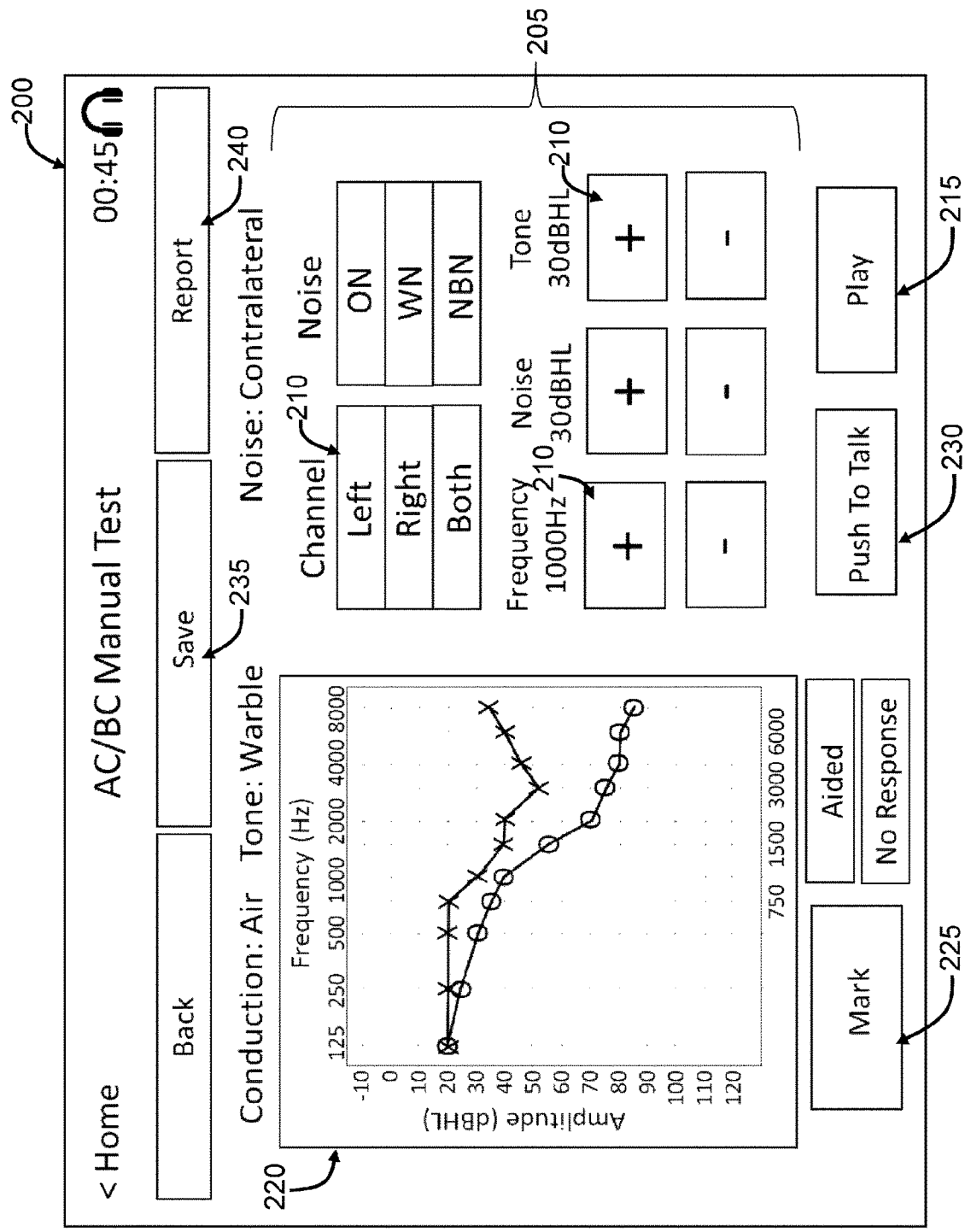
FIG. 2 illustrates a screenshot of a test screen of the system of FIG. 1, presented on the mobile audiometer device, according to an embodiment of the present invention.

FIG. 2 illustrates a screenshot 200 of a test screen of the system 100, presented on the mobile audiometer device 115, according to an embodiment of the present invention.

The test screen includes a test signal generation interface 205, which enables the audiologist to specify a test signal. The test signal interface 205 includes a plurality of buttons 210, to define the test signal, including channel buttons, for defining a channel (e.g. left or right) on which the test signal is generated, and noise type buttons, for defining a type of noise used on the test signal.

The test signal interface 205 further includes frequency buttons, for defining a frequency of the test signal, noise strength buttons, for defining a strength (amplitude) of the noise applied to the test signal, and tone strength buttons, defining a strength (amplitude) of the tone (test signal).

Once the audiologist 105 has defined the test signal, a play button 215 may be selected to cause the test signal to be played to the patient 110 on the transducer 120. The patient 110 then signals, e.g. using the trigger 130, whether he or she has heard the signal.

The audiologist 105 will go through a variety of test signals (tones) and use feedback from the patient 110 to generate an audiogram. The audiogram is displayed as it is generated in an audiogram element 220 of the test screen.

The audiogram complies with audiology standards, where the sounds heard in the right ear are marked in red, and sounds heard in the left ear are marked in blue. As such, the audiogram may be used directly in reports, and shared with other clinicians.

In some embodiments, when the patient presses the trigger 130, the audiogram is marked automatically for that frequency and amplitude. The test screen, however, further includes a mark button 225 to enable use where the patient 110 is unable to use the trigger, or in systems without a trigger. In such case, the patient 110 signals to the audiologist 105 by waving their hand (or any other suitable way), upon which the audiologist presses the mark button 225.

The audiologist 105 may have a microphone or headset to communicate with patient 110 in the soundproof room 135. In particular, the test screen further includes a talk button 230, upon which the audiologist 105 is able to communicate with the patient 110 on the transducer 120. In some embodiments, the soundproof room may include a microphone (not illustrated) allowing the patient 110 to communicate back to the audiologist 105. The microphone may be coupled to the mobile audiometer device 115 by the junction box 125.

When the audiologist 105 completes the test, a save button 235 may be selected. In such case, the captured data is stored on a data store, on the mobile audiometer device 115, or elsewhere.

A report button 240 is also provided to enable the audiologist 105 to generate a report relating to the test. The report is advantageously in a PDF or similar format, and may be saved on a data store, emailed, or stored or printed in any suitable way.

The report is generated using a template selected (or generated) by the audiologist 105. The system may enable the audiologist 105 to edit a template from the server. These features enable the audiologist 105 to use a letterhead of their choosing, and format the data according to their need. Furthermore, the report may be previewed by the audiologist 105 and electronically signed by the audiologist 105. In some embodiments the audiologist can select from custom pre-set sentences to assist in generating the report.

Turning back to FIG. 1, the mobile audiometer device 115 is also coupled to a remote server 140. This enables test data to be stored separate to the mobile audiometer device 115. This is particularly advantageous when the system 100 includes a plurality of mobile audiometer device 115, e.g. at various locations.

In one embodiment, the remote server 140 comprises an electronic health record (EHR) store, and stores EHRs of a plurality of patients 110, and from a plurality of audiologists 105. In addition to the test results described above, the EHRs may include other patient data, which may include OAE, tympanometry, and otoscopy data.

As EHRs are stored, the remote server 140 is generally compliant with the Health Insurance Portability and Accountability Act (HIPAA), or corresponding requirements in other jurisdictions.

The remote server 140, or the mobile audiometer device 115, may communicate with a common database or virtual server, for use by a plurality of fitting systems and suppliers. An example of such a database is the NOAH database of the Hearing Instrument Manufacturers' Software Association (HIMSA) of Copenhagen, Denmark. This enables the test results of a hearing test to be used directly in programming hearing aids, for example.

The mobile audiometer 115 generates the test signals (e.g. test tones) using software, and without requiring any external hardware. In particular, the mobile audiometer 115 includes a Tone Generator Engine (TGE) to produce highly consistent test signals. In particular, the test tones and test noises are generated with great accuracy in both frequency and amplitude. The TGE uses frameworks or APIs that interface with the hardware of the mobile audiometer device 115 to generate stimuli, including tone and noise and speech stimuli. This enables the TGE to generate very accurate and consistent test signals. The frameworks and APIs used may be provided in the operating system which runs on the mobile audiometer 115, and examples of frameworks and APIs include the "AudioUnit" framework available on Apple® iOS® devices, and the AAudio APIs available for Google® Android® devices.

The mobile audiometer 115 further includes advanced digital processing of audiology speech material, which includes an adaptive algorithm to detect when a "word" is played. The TGE then controls the characteristic of the stimulus being emitted based upon whether or not a word is detected.

In particular, the TGE processes in real time the speech material as follows.

While the speech material (e.g. from an audio file) is being played, the TGE measures the amplitude level thereof and generates (and updates) an average amplitude value at a determined sampling frequency (e.g. 0.5 seconds).

The TGE then compares each new measured amplitude level of the speech material to the current average amplitude value. In the case of new measured amplitude is not statistically correlated to the average amplitude value or the new measured amplitude value falls outside a tolerance range around the average amplitude value, the TGE triggers the event of "a word is being played". Otherwise, the TGE updates the average amplitude value at the determined sampling frequency (e.g. 0.5 seconds);

When "a word is being played" event is identified, the mobile audiometer 115 visually notifies the audiologist. As such, the system 100 allows the audiologist to use any speech material without having to worry about listening to the audio and manually tracking each word which has been played.

The TGE may control the stimulus according to a time to rise/fall, cross talk, or harmonic distortion, for example. This can be done applying to the stimuli a set of well-known digital filters or ad hoc designed digital filters to control the output. As an illustrative example, the TGE may apply a counter-phase signal filter on transducers not in use to mitigate or eliminate unwanted stimuli to control cross talk.

In some embodiments, the TGE can use existing APIs and frameworks available on the operative system running on the mobile audiometer 115, such as the "Speech Recognition API" available for Apple® iOS® devices, to automatically transcribe words that are played, and independently from the language of the audio file. This gives to the audiologist a very important benefit: they can use any speech material in any language without worrying about manually writing the words list.

The consistency and accuracy provided by the TGE enables the mobile audiometer 115 to be calibrated to international audiological standards, such as ANSI and EN standards. Furthermore, the TGE simplifies calibration (e.g. for each pair of a plurality of transducers) as it enables a single changed amplitude (used as "starting amplitude value") for a frequency to be used to make relative amplitude changes for all the amplitudes which belong to that frequency. As such, instead of calibrating each amplitude (from −10 to 120 dBHL) for each stimulus (125 to 20000 Hz), the TGE enables calibration based upon one amplitude change for each frequency. The TGE also enables us an external pre-recorded audio file to be used to calibrate speech material for speech testing.

The TGE operates on float values (any real coefficient from 0 to 1) when generating stimuli using the abovementioned APIs and Frameworks. For each transducers and for each frequency, a starting float value is empirically found for a certain starting Y dBSPL value and stored as "(Float Value for Y dBSPL)$_i$,", where i is the i-th frequency supported by that transducer. This is done for all of the channels for each transducer (i.e. Left Speaker, Right Speaker). Then, the TGE uses the following algorithm to calculate the float value corresponding to the desired X dBSPL value starting from "(Float Value for Y dBSPL)$_i$":

$$(\text{Float Value for } X \text{ dBSPL})_i = (\text{Float Value for } Y \text{ dBSPL})_i * 10 \text{ pow}((X-Y)/20)_i$$

In short, the system 100 provides a cost-effective hearing evaluation system to diagnose hearing impairments in patients. By utilising the mobile audiometer 115, the system 100 is easy to set up and move, as required.

Figure 3:
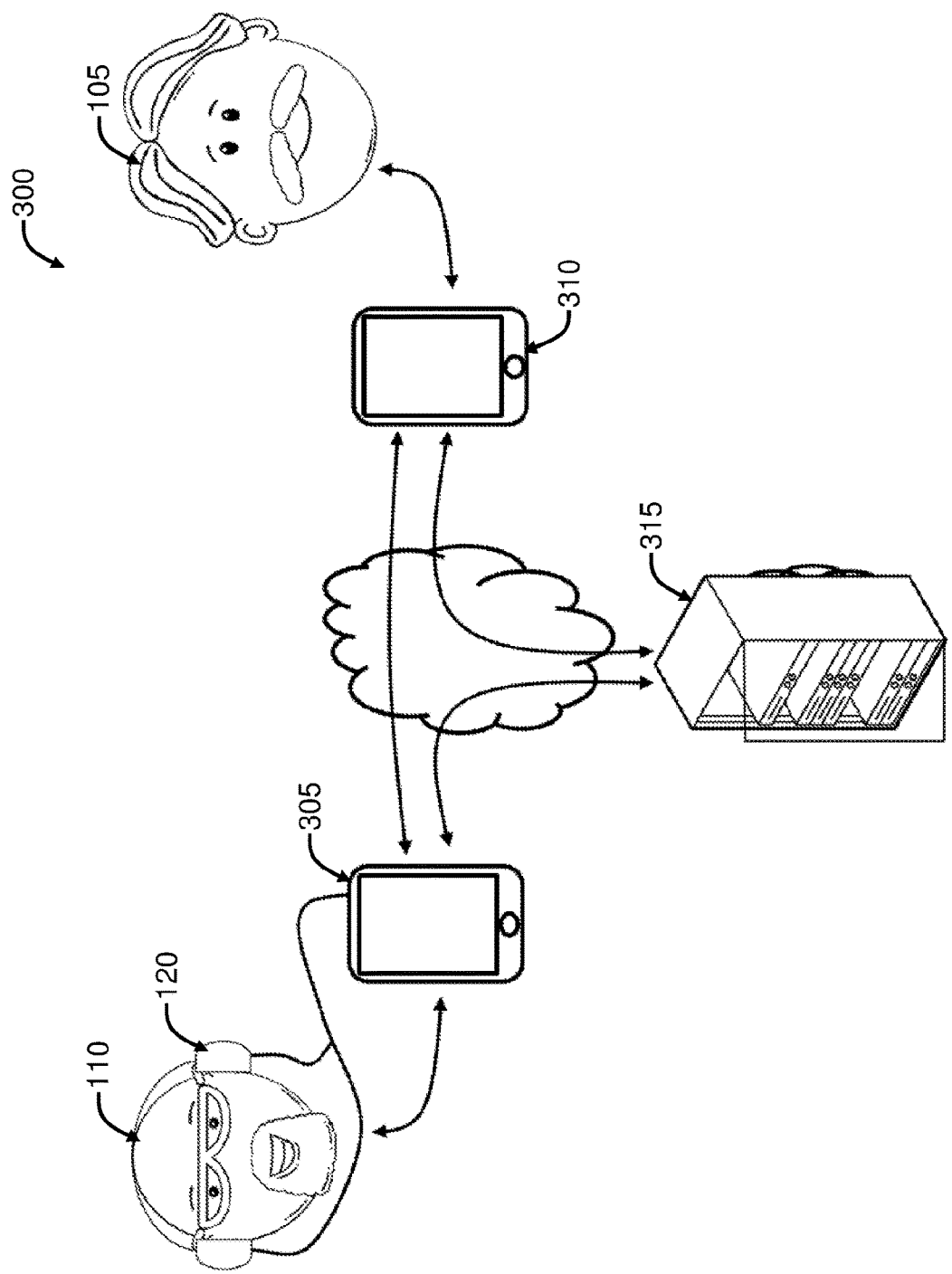
FIG. 3 illustrates a hearing evaluation system, according to an embodiment of the present invention.

The system 100 may be modified to provide remote audiometry services, as outlined below. In particular, FIG. 3 illustrates a hearing evaluation system 300, according to an embodiment of the present invention. The system 300 enables audiometry services, similar to those provided by the system 100, to be provided remotely.

The system 300 includes a patient audiometer device 305, with which the patient 110 interacts. In particular, the transducer 120 is coupled to the patient audiometer device 305 and is used to present test signals to the patient 110.

The audiologist 105 interacts with a remote audiometer device 310, which communicates directly with the patient audiometer device 305 via a communications network, such as WAN, LAN, cellular or satellite networks.

The patient audiometer device 305 and the remote audiometer device 310 function in a manner similar to the mobile audiometer device 115, albeit split over several locations. However, in addition to the features of the mobile audiometer device 115, video and audio communication is provided between the remote audiometer device 310 and the patient audiometer device 305 to enable communication between the patient 110 and the audiologist 105.

The audiologist 105 interacts with the remote audiometer device 310 in a similar manner to that describe above with reference to the mobile audiometer device 115. In particular, the audiologist 105 selects or enters the patient's details, and performs one or more tests.

Figure 4:
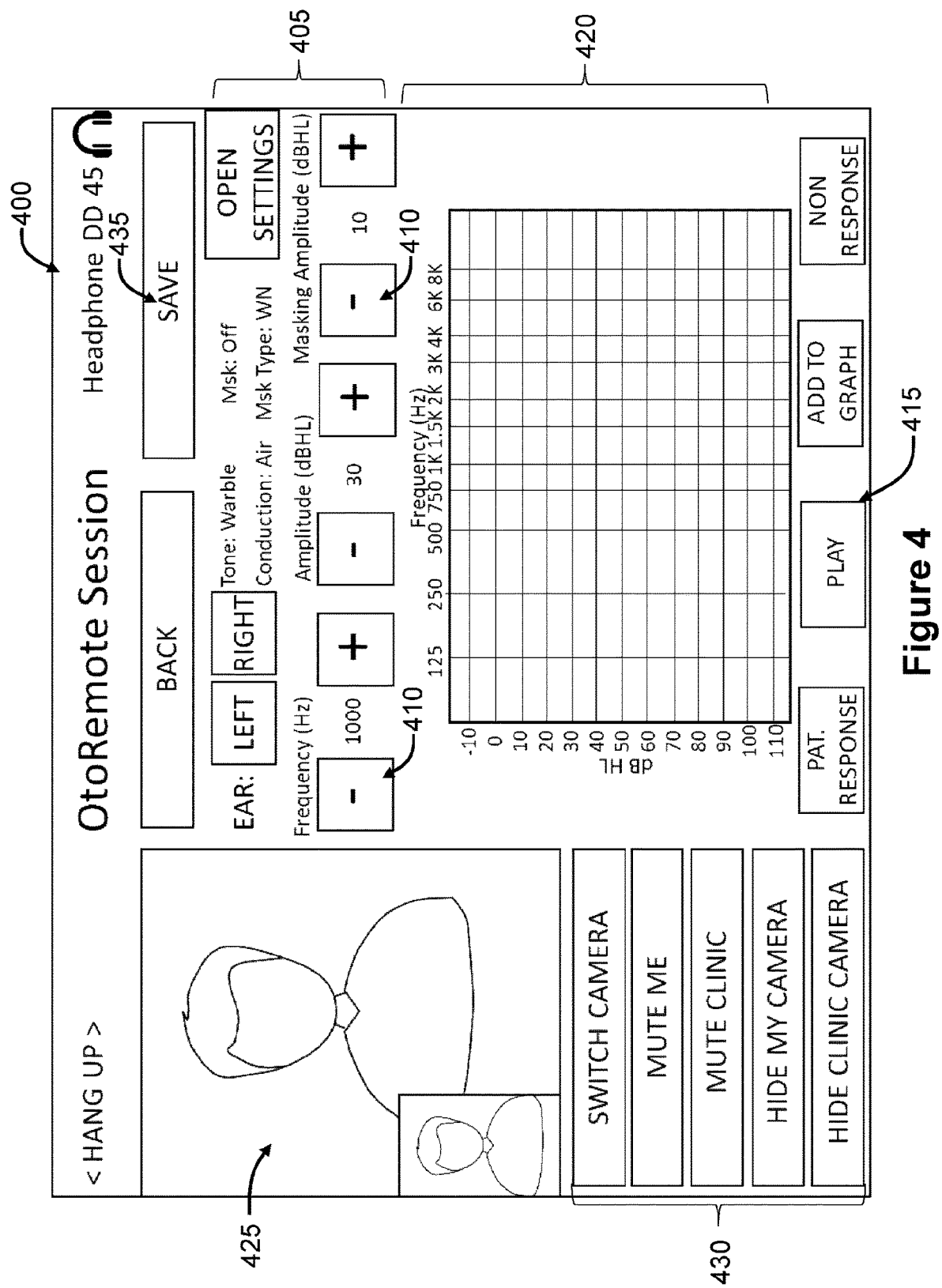
FIG. 4 illustrates a screenshot of a test screen of the system of FIG. 3, according to an embodiment of the present invention.

FIG. 4 illustrates a screenshot 400 of a test screen of the system 300, according to an embodiment of the present invention.

The test screen is similar to the test screen of FIG. 2, but includes remote communications capabilities.

In particular, the test screen includes a test signal generation interface 405, which enables the audiologist to specify a test signal, much like the test signal generation interface 205, using a plurality of buttons 410, including frequency buttons, noise (masking) strength buttons, and tone strength buttons.

Once the audiologist 105 has defined the test signal a play button 415 may be selected to cause the test signal to be played to the patient 110 on the transducer 120. In such case, a message is sent from the remote audiometer device 310 to the patient audiometer device 305, defining the test signal. A TGE on the patient audiometer device 305 then generates and plays the test signal.

The patient 110 then signals, using a button on the patient audiometer device 305, whether he or she has heard the signal, and the results (i.e. when the patient 110 heard the test signal) is then sent to the remote audiometer device 310, upon which an audiogram is generated, and displayed in an audiogram element 420, similar to the audiogram element 220.

Both the patient audiometer device 305 and the remote audiometer device 310 include a camera, microphone and speakers, which enables the audiologist 105 and the patient 110 to communicate directly with each other.

In this regard, the test screen includes a videoconferencing element 425, which includes an image of the patient 110 (as captured by the camera of the patient audiometer device 305) and an image of the audiologist 105 (as captured by the camera of the remote audiometer device 310).

The test screen includes a videoconferencing menu 430, which enables the audiologist 105 to configure the videoconferencing aspects of the system 300, such as which camera is used on the remote audiometer device 310, and whether microphones and cameras are shown/muted or not.

When the audiologist 105 completes the test, a save button 435 may be selected, as outlined above. In such case, the captured data is transmitted to a remote server 315 for storage. Similarly, patient data may be transmitted from the patient audiometer device 305 to the remote server 315 for storage.

A report button (not shown) may also be provided to enable the audiologist 105 to generate a report relating to the test, as outlined above.

The system 300 provides high quality, remote hearing tests to be performed. As the patient audiometer device 305 and the remote audiometer device 310 communicate directly with each other, and the TGE resides on the patient audiometer device 305, high quality audiometric testing may be performed even on a very-low bandwidth network connection.

In some embodiments of this invention, the remote audiometer device 310 (used by the audiologist) can be coupled to multiple patient audiometer devices 305 simultaneously, and a direct video and audio communication link may be established with multiple patient audiometer devices 305 at the same time.

As will be readily understood by the skilled addressee, the system 300 will include other authentication features, such as authentication of the patient 110 and the audiologist 105, to prevent unauthorised access to the system 300.

The systems 100 and 300 may utilise a switch box, coupled to a plurality of transducers, to enable automatic and/or remote switching between transducers, without having to unplug and plug in the transducers.

Figure 5:
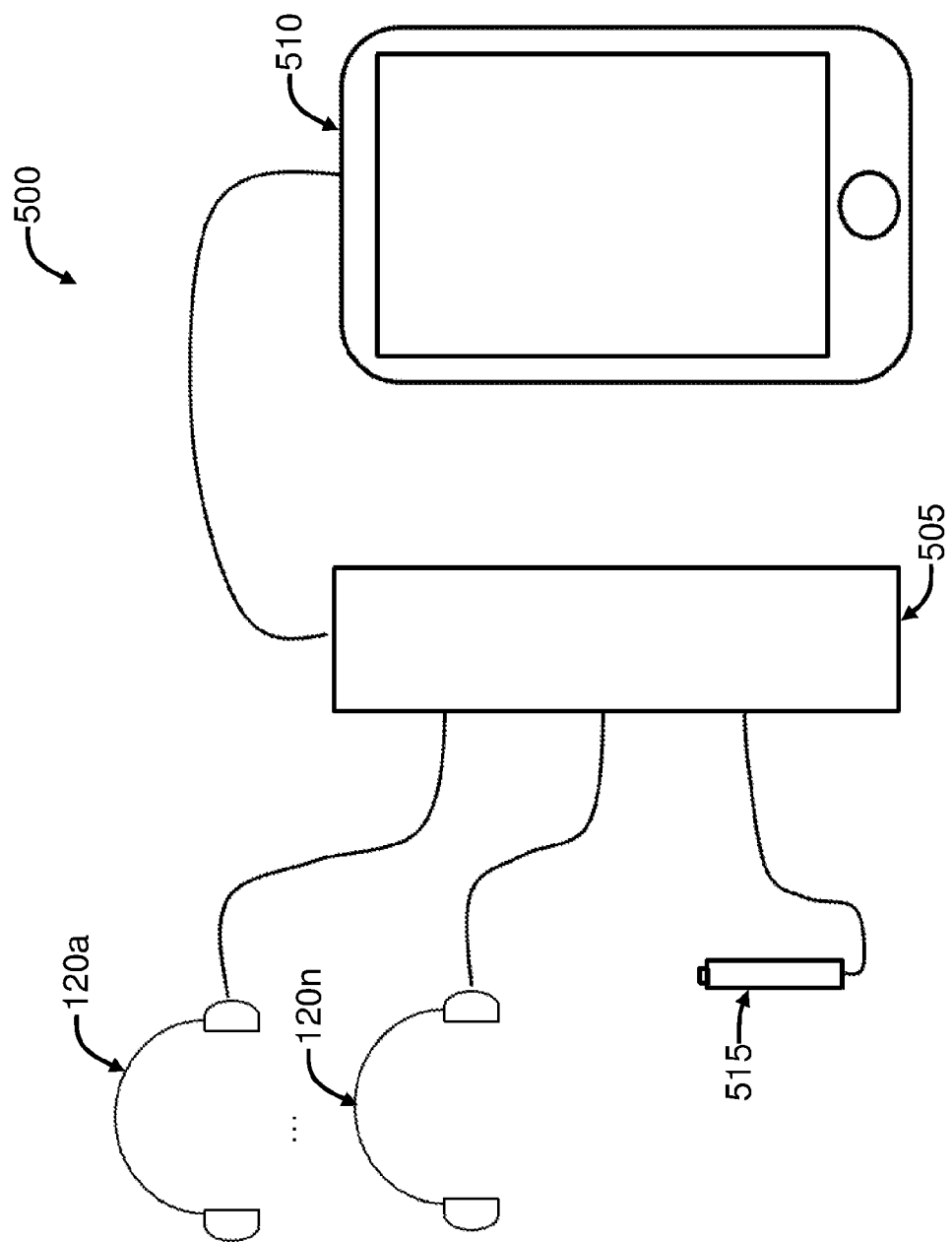
FIG. 5 illustrates a switched hearing evaluation system, for diagnosing hearing impairments, according to an embodiment of the present invention.

FIG. 5 illustrates a switched hearing evaluation system 500, for diagnosing hearing impairments, according to an embodiment of the present invention. The hearing evaluation system 500 may be similar to the system 100 or a patient portion of the system 300, but enables multiple transducers 120a-120n to be coupled simultaneously.

The system 500 includes a switch box 505 coupled to a mobile audiometer device 510. The mobile audiometer device 510 may be similar or identical to the mobile audiometer device 115 or the patient audiometer device 305.

A plurality of transducers 120a-120n are simultaneously coupled to the switch box 505, and the mobile audiometer device 510 communicates with the switch box 505 to activate a transducer 120a-120n. An output of the switch box 505 couples the activated transducer 120a-120n to the mobile audiometer device 510.

In particular, a wireless link is created between the mobile audiometer device 510 and the switch box 505, and the mobile audiometer device 510 indicates on the wireless link which of the transducers 120a-120n should be activated. The switch box 505 then activates one or more internal switches or relays to couple the activated transducer 120a-120n to the output, and thus the mobile audiometer device 510.

The switch box 505 allows testing to be carried out using several transducers, without requiring the transducers to be plugged in or unplugged, and with minimal interruption.

The switch box 505 is also coupled to one or more input devices 515, such as a trigger (patient response button), or a microphone. The switch box 505 may communicate data from the input devices 515 wirelessly.

In one embodiment of the invention, the switch box 505 can is configured to be connected to an air transducer and a bone vibrator and easily switch between these via hardware or via software interface. In another embodiment, the switch box 505 allows connection of three transducers at the same time, a patient response hardware button, a patient microphone (enabling communication from inside a soundproof booth) and a clinician headset.

In addition to the remote testing scenarios described above, embodiments of the invention may be used to provide kiosk-like services at pharmacies and health centres. In such case, the systems may provide a low cost way of performing hearing tests, and to generate qualified leads for clinical practices. In certain cases, a shopping cart may be provided in association with the testing to sell hearing products.

Figure 6:
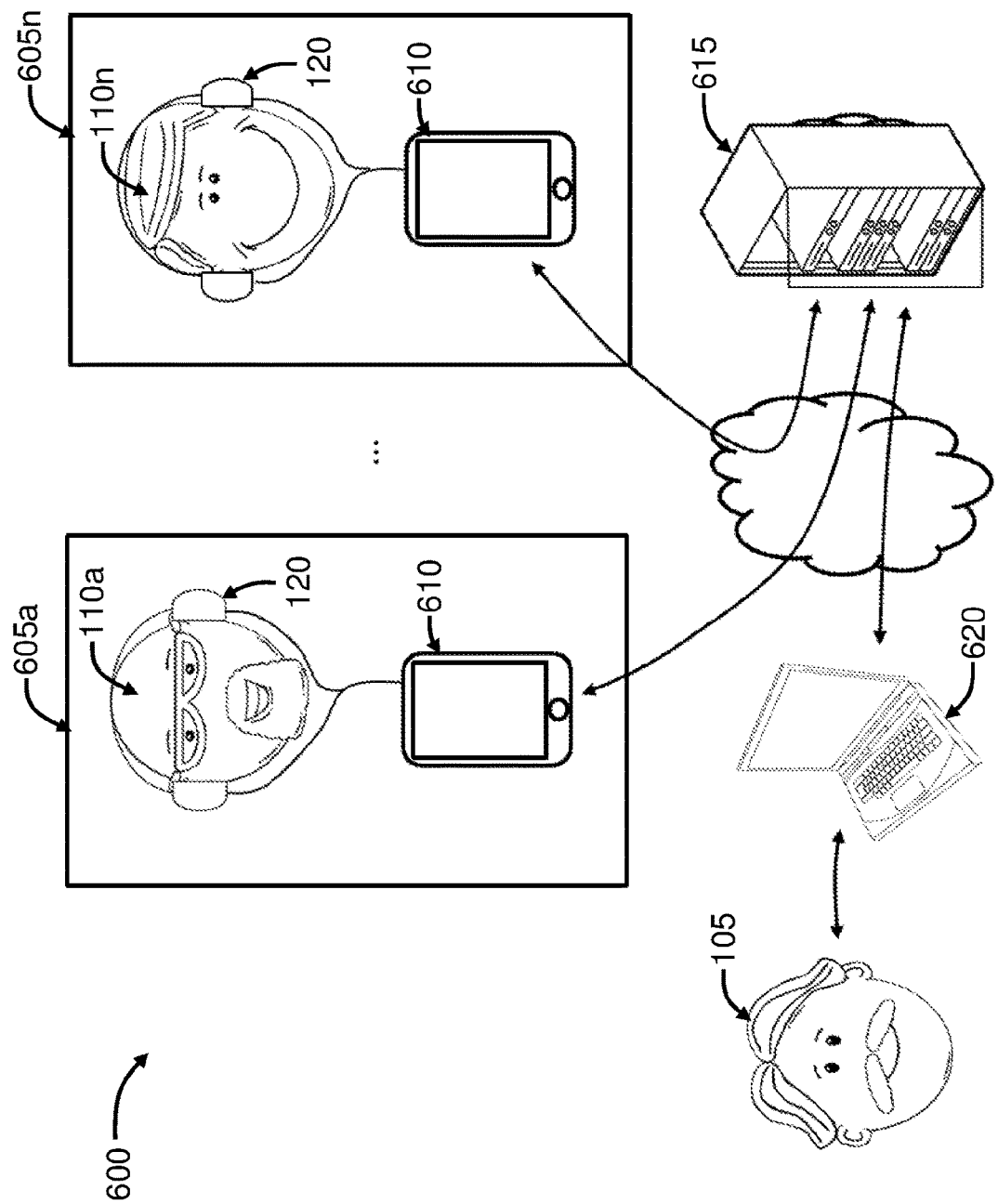
FIG. 6 illustrates a hearing evaluation system, for diagnosing hearing impairments, according to an embodiment of the present invention.

FIG. 6 illustrates a hearing evaluation system 600, for diagnosing hearing impairments, according to an embodiment of the present invention. The hearing evaluation system 600 is spread over a variety of areas, such as kiosks in pharmacies.

The system 600 enables a single audiologist (or other professional) to manage a plurality of hearing evaluation kiosks 605a-605n, which may be located in a wide area (e.g. across a city, state or country). In short, self-service testing is provided at each of the hearing evaluation kiosks 605a-605n.

Each hearing evaluation kiosks 605a-605n includes a mobile audiometer device 610, in the form of a tablet computer including software thereon, configured to provide audiometric testing. The mobile audiometer device 610 is similar to the mobile audiometer device 115, but is configured to guide the patient through audiometric testing procedures.

In use, a transducer 120 is worn by the patient 110, the transducer 120 coupled to the mobile audiometer device 610, and a sequence of testing procedures is presented to the patient 110a-n. The patient 110a-n initiates the test and provides feedback by interacting with the mobile audiometer device 610 directly. Testing is carried out according to the Hughson-Westlake method, and the devices 610 are calibrated according to international audiological standards, with results sufficiently reliable to allow for clinical standards of review and diagnosis.

In some embodiments, the kiosk can perform automated pure tone testing, automated speech testing and/or automated speech in noise testing. Furthermore, in some embodiments, the kiosk can provide manual diagnostic hearing assessment: this option can be enabled locally kiosk by kiosk, or remotely from the server 615.

In some embodiments, the kiosk can ask the patient to pay a fee to conduct the hearing assessment ("Pay per Test"). The amount of that fee can be set remotely by the audiologist.

Once the test is complete, and the patient 110a-110n has entered his or her details, results of the test are uploaded to a server 615 for storage and evaluation. The collection of patient data may occur before the hearing test is performed.

The server 615 is accessible by the audiologist 105 through a computing device 620, where data is able to be reviewed and further consultation booked, if required.

The audiologist 105 may thus remotely manage the kiosks 605a-605n, and allocate leads therefrom.

On the server 615 a web portal is provided which allows the audiologist to have full remote live control over the whole system. The audiologist can see a map where all the kiosks 605a-605n are located in real time. Furthermore, the audiologist can access details of each kiosk and perform customisation remotely, such as, changing a logo, enabling/disabling custom or standard features, associating hearing products to be sold using the store functionality, and enabling/disabling the "Pay per Test" feature.

The audiologist using the web portal can have access to the latest patient data collected, perform data filtering and data exporting. Data exporting can be as printable information (such as PDF) or as universal file format (such as CVS file format) or as data securely transmitted to external software (for example via HTTPS protocol to third party APIs).

The said web portal may be developed using a combination of server programming languages (such as NodeJS) and database programming languages (such as MySQL). Furthermore, the web portal and its server 615 is compliant with privacy regulations, such as HIPAA.

According to certain embodiments, the kiosks 605a-605n are configured to auto detect their locations, send this location data in background to the server 615. The kiosks 605a-605n may also automatically determine the closest server location available based upon their location, and interact with the closest server (which is particularly useful in case multiple servers like the 615 are placed across the world). The skilled addressee will readily appreciate that this solution will allow the system to be easily complaint with Privacy Regulations, assuring that the data collected in a country are stored within that country.

According to certain embodiments, the hearing results are used to determine suitable hearing products, and the benefits of the hearing products will be presented. At the same time, the patient may be referred to an audiologist or other health professional and book an appointment directly from the kiosk.

From the server 615 and its web portal, the audiologist can add information about his offices locations and contact information which will be presented to the patient at the end of the hearing test.

In some embodiments of the invention, the mobile audiometer device 610 presents a section where a hearing enhancement simulation is provided. This section allows the patient to evaluate which benefits a hearing product can bring.

The hearing enhancement simulation performs digital audio processing in real time of some samples audio files (i.e. a recorded speech played against different noisy environments, such as, but not limited to: cocktail party, restaurant, church, at home with the TV on etc.) or of live ambient sounds, using as audio filter a Hearing Aids Fitting Rationale Formula (such as, but not limited to: NAL-R). The formula uses as input the hearing thresholds obtained during the test (i.e. the dBHL values).

The Hearing Aids Fitting Formula can be set remotely by the audiologist using the server 615 or automatically associated by the server 615 to the mobile audiometer device 610 when a hearing product is associated to the said mobile audiometer device 610 for the purpose of being sold through the store, as outlined below.

According to certain embodiments, the mobile audiometer devices 610 include noise control, which enables the kiosks to be developed without soundproof chambers.

In particular, the mobile audiometer devices 610 monitor ambient noise and determine whether test conditions are permissible. This may be transducer specific, and thus based on the noise insulation provided by the transducers being used.

The mobile audiometer devices 610 may then delay or repeat testing based on noise levels, or even abandon testing when background noise is high.

According to certain embodiments, the mobile audiometer devices 610 may compensate or adjust test results based upon the level of background noise experienced at the moment that the test stimulus was presented.

These capabilities make the system 600 suitable for use in a wide range of noisy environments, opening up the possibility of providing reliable audiometric testing without soundproof booths.

In particular, the system 600 can implement a noise compensation algorithm which performs measurements in narrowband or broadband of the background noise while the stimuli is being presented to the patient and use these noise measurements to compensate each hearing loss result. The compensation algorithm used in this case is:

$$(\text{Compensated dBHL})_i = (\text{Uncompensated dBHL})_i + a_i * (\text{Noise Contribution dBSPL})_i$$

where:
- (Compensated dBHL)$_i$ represents the new compensated hearing loss level at the i-th frequency under testing;
- (Uncompensated dBHL)$_j$ represents the hearing loss level at the i-th frequency under testing reported by the Patient interacting with the mobile audiometer device 610;
- $a_i$ is a real coefficient specific for each i-th frequency;
- (Noise Contribution dBSPL)$_i$ represents the dBSPL measures of the noise. In the case of broadband measures, these contribution values are interpolated, whist in the case of narrowband measures centered at the stimulus frequency, these contribution values are the actual values measured.

The above-mentioned noise measurements can be performed using the built-in microphone of the mobile audiometer device 610 or by pairing the latter with an external professional microphone.

While the system 600 is described with reference to the used with reference to the audiologist 105, the skilled addressee will readily appreciate that the system 600 may be adapted to provide testing without any professional intervention. The system 600 may also be configured to enable a client to purchase products based upon the test results in a built-in store or in an external online store.

The audiologist can indeed associate a hearing product individually to each kiosk, using the web portal available on the server 615. It is possible to select a picture for the hearing product, select or upload a Hearing Aids Fitting Rationale (used for the hearing enhancement section), set the price for 1 item or for 2 items and decide whether to accept monthly payments or one-off payments. The skilled addressee will readily appreciate that this functionality will allow the audiologist to provide bespoke hearing product solutions basing on territory overcoming the big current hurdle of providing valuable hearing healthcare access to the hearing impaired.

Furthermore, in addition to a hearing product, the audiologist can associate to each kiosk in the same way as above with hearing services (such as follow-up appointments) and hearing product related products (such as batteries, cleaning tools).

According to certain embodiments, the systems 100, 300 and 600 may be used with "ear bud" headphones, which have been calibrated to one or more audiometric standards. This enables testing to be carried out using off-the-shelf ear bud products, rather than expensive audiometric transducers.

According to certain embodiments, the systems 100, 300 and 600 are used with transducers that provide both passive noise insulation, together with active electronic noise cancellation. The combination of active and passive noise insulation and cancellation control further assists in providing accurate testing in environments outside a soundproof booth.

According to certain embodiments, the remote test systems described above may be integrated with remote fitting procedures. In particular, the both testing and fitting may be carried out seamlessly using the same device.

In particular, testing is first performed to determine the patients hearing loss, as outlined above, and at various frequencies. This information is then used to program a hearing device by adjusting the amplitude to accord with the patients tested hearing loss at each frequency.

Furthermore, in some embodiments, a hearing product (e.g. a hearing aid) may be used directly in the systems described above in place of the transducer. The test outcomes are then used to program the hearing product, which is fitted to the patient, and may be subsequently fine-tuned.

Figure 7:
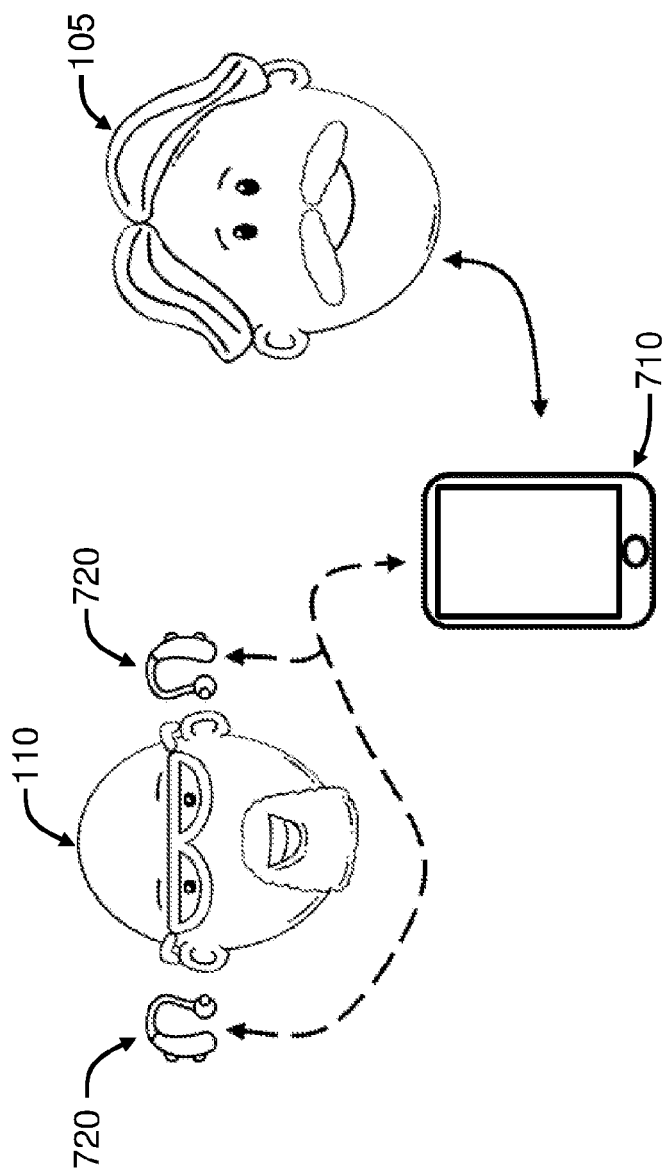
FIG. 7 illustrates a hearing device fitting system, according to an embodiment of the present invention.

FIG. 7 illustrates a hearing device fitting system 700, according to an embodiment of the present invention. The system utilises a hearing device 720 that is initially neutrally programmed (no compensating amplification at any frequencies), which is used for both testing and configuration. This effectively merges testing and fitting, which are traditionally performed separately, which in turn provides greater efficiency and accuracy, as well as added convenience to the patient.

In particular, the hearing device 720 is initially used for hearing tests, in a similar manner to how the transducer 120 is used, as described above. This is achieved using a mobile audiometer device 710, similar to the mobile audiometer device 115, but configured to test using the hearing device 720 which is being fitted. The hearing device 720 may be wirelessly (or wiredly) coupled to the mobile audiometer device 710 for such purpose.

In use, the hearing device 720, which may comprise a single or multiple hearing aids, is worn by the patient 110 in a default state. A plurality of test signals are generated on the mobile audiometer device 710 under instruction from an audiologist 105, and then provided to the patient on the hearing device 720, in a similar manner to that described above with reference to the transducer 120. Feedback is provided by the patient 110, which is used to generate a hearing profile for that patient 110.

The hearing device 720 is then updated according to the hearing profile of the patient 110. This may include amplifying one or more frequencies based upon the hearing profile. Further tests may be performed on the hearing device 720, to iteratively tune the hearing device 720.

The mobile audiometer device 710 may be configured to monitor ambient noise levels, and adjust the hearing tests according to the ambient noise levels. Furthermore, the mobile audiometer device 710 may be configured to repeat one or more tests (and discard certain test results) if ambient noise levels go above a certain threshold.

While the system 700 is controlled by an audiologist 105, the skilled addressee will readily appreciate that the system 700 may be automated, or controlled by the patient 110. This is particularly useful in case the patient 110 is configuring his or her own hearing aid.

Once the testing has been completed, and the hearing device 720 is configured, the configuration may be saved for future reference. In this regard, the mobile audiometer device 710 may be configured to upload the configuration data to a remote server.

The mobile audiometer devices described above advantageously includes a touch screen, with which the audiologist 105 or patient 110 interacts. The skilled addressee will, however, readily appreciate that any suitable type of data input or user interface may be used, including a physical keyboard and mouse.

While the mobile audiometer 115 is described as a tablet computer, in alternative embodiments the mobile audiometer 115 comprises a smartphone, a laptop, a smartwatch, smart speakers, or any other suitable portable computing device.

The transducers described above may be any suitable type of transducer, including air conduction and bone conduction transducers. Examples of suitable transducers include TDH39, TDH49, DD45, ER3A, ER5A, ER3C, IP30 and B71W transducers.

Any suitable audiometric testing may be performed using the systems described above, including AC/BC and masking, speech, soundfield, tinnitus evaluation and additional pure tone testing.

Advantageously, the systems may be calibrated to internationally accepted audiological standards (incl ANSI and ISO-EN), and thus provide consistent and reliable test results.

The systems are advantageously portable, and as such may be used in remote areas that previously have not received audiological services.

By utilising tablet computers, or similar devices, updates to the system are enabled by software and without requiring hardware changes.

By enabling reports to be generated automatically, the audiologists are able to use their time more efficiently.

Noah integration enables the systems to be easily used together with the programming of hearing devices.

Embodiments of the present invention enable accurate remote testing, which reduces the need for travel, particularly for those in remote communities. The point-to-point communication provided by such embodiments enables high accuracy even when bandwidth is low.

Self-service testing provides opportunities for patients to conduct hearing tests in conjunction with other medical services, such as when at a pharmacy. Together with ambient noise controls the system may be used to in such situations without requiring a soundproof booth.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A portable hearing evaluation system including: a portable computing device configurable to provide audiometric testing of a patient using each of a plurality of transducers that are releasably couplable to the portable computing device and according to one or more audiological standards; and a transducer, of the plurality of transducers, releasably coupled to the portable computing device, wherein the portable computing device comprises a Tone Generator Engine (TGE) configured to generate, at the portable computing device, a plurality of test signals comprising test tones for providing calibrated audiometric testing of the patient using the transducer, the plurality of test signals generated at least in part according to both 1) one or more input parameters defining at least a frequency and/or amplitude of the test signal and 2) the calibration data for the transducer, such that the plurality of test signals are calibrated for the transducer, and provide, on an output of the portable computing device, the plurality of test signals for playback on the transducer, wherein the TGE is configurable to use different pre-generated calibration data for each of the plurality of transducers, and wherein the pre-generated calibration data for each of the plurality of transducers is stored locally on the portable computing device or remotely on a server.

2. The portable hearing evaluation system of claim 1, further comprising a trigger, for use by the patient, to signal that he or she has heard a test signal.

3. The portable hearing evaluation system of claim 2, wherein the trigger comprises a button on a graphical user interface.

4. The portable hearing evaluation system of claim 1, wherein the TGE is configured to detect when the test signal comprises a word, and adjust an output on the transducer according to whether the word is detected.

5. The portable hearing evaluation system of claim 1, wherein the TGE is configured to calibrate the portable computing device to the transducer by extrapolating an amplitude change for a single amplitude across a plurality of amplitudes.

6. The portable hearing evaluation system of claim 1, wherein the portable computing device includes a user interface and wherein the user interface enables an audiologist to specify characteristics of the plurality of test signals.

7. The portable hearing evaluation system of claim 1, wherein the portable computing device includes a user interface and wherein the portable computing device is configured to generate an audiogram based upon patient responses, wherein the user interface includes the audiogram.

8. The portable hearing evaluation system of claim 1, further comprising a soundproof booth, wherein the patient is located within the soundproof booth during testing, and the portable computing device may be located outside of the soundproof booth.

9. The portable hearing evaluation system of claim 1, wherein the system is configured to provide remote audiometric testing of the patient, the system including a remote computing device, coupled to the portable computing device, wherein the remote computing device is configured to be used by an audiologist.

10. The portable hearing evaluation system of claim 9, wherein the remote computing device is configured to send parameters to the portable computing device defining a test tone, wherein the portable computing device is configured to generate the test tone based upon the parameters.

11. The portable hearing evaluation system of claim 9, wherein the portable computing device is configured to receive input from the patient regarding whether or not the patient has heard the test signal, and submit the input to the remote computing device.

12. The portable hearing evaluation system of claim 9, wherein the portable computing device and the remote computing device are configured to communicate with each other directly, and if direct communication is interrupted, communicate through a server.

13. The portable hearing evaluation system of claim 1, wherein data of audiometric testing is used to program a hearing product.

14. The portable hearing evaluation system of claim 1, wherein the system includes a switch box, configured to couple one or more of the plurality of transducers to the portable computing device.

15. The portable hearing evaluation system of claim 14, wherein the switch box includes a wired or wireless connection with the portable computing device on which the plurality of test signals are received, and a control link with the portable computing device on which control signals are received, the control signals used to activate a particular transducer of the plurality of transducers.

16. The portable hearing evaluation system of claim 1, wherein the system is configured to detect background noise, and either 1) determine whether test conditions are acceptable based on the background noise or 2) make compensating adjustments to test data based upon the background noise.

17. The portable hearing evaluation system of claim 16, further configured to detect narrowband background noise defined around a central frequency for each of a plurality of stimuli frequencies.

* * * * *